US007608580B2

(12) United States Patent
Kim et al.

(10) Patent No.: US 7,608,580 B2
(45) Date of Patent: *Oct. 27, 2009

(54) INJECTABLE CARRIER FORMULATIONS OF HYALURONIC ACID DERIVATIVES FOR DELIVERY OF OSTEOGENIC PROTEINS

(75) Inventors: Hyun Kim, Middleton, MA (US); Rebecca Li, Bedford, MA (US); Alessandra Pavesio, Padua (IT); Lanfranco Callegaro, Thiene (IT); Howard Seeherman, Cambridge, MA (US); John Wozney, Hudson, MA (US)

(73) Assignees: Genetics Institute, LLC, Cambridge, MA (US); Fidia Advanced Biopolymers S.R.L., Abano Terme, Padua (IT)

( * ) Notice: Subject to any disclaimer, the term of this patent is extended or adjusted under 35 U.S.C. 154(b) by 56 days.

This patent is subject to a terminal disclaimer.

(21) Appl. No.: 11/624,463

(22) Filed: Jan. 18, 2007

(65) Prior Publication Data

US 2007/0134342 A1   Jun. 14, 2007

Related U.S. Application Data

(63) Continuation of application No. 09/687,281, filed on Oct. 13, 2000, now Pat. No. 7,189,392.

(60) Provisional application No. 60/159,674, filed on Oct. 15, 1999, provisional application No. 60/185,587, filed on Feb. 28, 2000.

(51) Int. Cl.
  *A61K 38/16* (2006.01)
(52) U.S. Cl. ......................................................... 514/2
(58) Field of Classification Search ................. None
  See application file for complete search history.

(56) References Cited

U.S. PATENT DOCUMENTS

| 3,955,719 | A | 5/1976 | Pheulpin |
| 4,758,233 | A | 7/1988 | Phillips et al. |
| 4,784,055 | A | 11/1988 | Langen et al. |
| 4,851,521 | A | 7/1989 | della Valle et al. |
| 4,957,744 | A | 9/1990 | della Valle et al. |
| 5,118,667 | A | 6/1992 | Adams et al. |
| 5,124,316 | A | 6/1992 | Antoniades et al. |
| 5,290,271 | A | 3/1994 | Jernberg |
| 5,308,889 | A | 5/1994 | Rhee et al. |
| 5,324,775 | A | 6/1994 | Rhee et al. |
| 5,328,955 | A | 7/1994 | Rhee et al. |
| 5,336,767 | A | 8/1994 | della Valle et al. |
| 5,352,715 | A | 10/1994 | Wallace et al. |
| 5,356,629 | A | 10/1994 | Sander et al. |
| 5,413,989 | A | 5/1995 | Ogawa et al. |
| 5,422,340 | A | 6/1995 | Ammann et al. |
| 5,464,440 | A | 11/1995 | Johansson |
| 5,510,121 | A | 4/1996 | Rhee et al. |
| 5,645,592 | A | 7/1997 | Nicolais et al. |
| 5,658,882 | A | 8/1997 | Celeste et al. |
| 5,752,974 | A | 5/1998 | Rhee et al. |
| 5,935,594 | A | 8/1999 | Ringeisen et al. |
| 5,939,323 | A | 8/1999 | Valentini et al. |
| 5,942,499 | A | 8/1999 | Radomsky |
| 6,132,214 | A | 10/2000 | Suhonen et al. |
| 6,187,742 | B1 | 2/2001 | Wozney et al. |
| 6,699,471 | B2 | 3/2004 | Radice et al. |
| 7,189,392 | B1 | 3/2007 | Kim et al. |

FOREIGN PATENT DOCUMENTS

| CZ | 283073 B6 | 12/1997 |
| JP | 2000-202024 | 7/2000 |
| WO | WO 91/17777 | 11/1991 |
| WO | WO 93/20858 | 10/1993 |
| WO | WO 97/32591 | 9/1997 |
| WO | WO 97/45532 | 12/1997 |
| WO | WO 97/49412 | 12/1997 |
| WO | WO 99/24070 | 5/1999 |
| WO | WO 00/16818 | 3/2000 |
| WO | WO 00/37124 | 6/2000 |
| WO | WO 02/43759 | 6/2002 |

OTHER PUBLICATIONS

Fleisch, Bisphosphonates In Disease, From the Laboratory to the Patient, 3rd Ed. Parthenon Publishing (1997).
International Search Report for PCT/US00/28468.
Notice of Revocation of EP1223990.
Aigner et al., "Cartilage tissue engineering with novel nonwoven structured biomaterial based on hyaluronic acid benzyl ester," J Biomed Mater Res 42:172-181 (1988).
Bonucci et al., "Prevention of Ovariectomy Osteopenia in Rats after Vaginal Administration of Hyaff 11 Microspheres Containing Salmon Calcitonin," Calcif Tissue Int 56:274-279 (1995).
Brun et al., "Chondrocyte aggregation and reorganization into three-dimensional scaffolds," J Biomed Mat Res 46:337-46 (1999).
Campoccia et al., "Semisynthetic resorbable materials from hyaluronan esterification," Biomaterials, 19:2101-27 (1998).
Ghezzo et al., "Hyaluronane derivative microspheres as NGF delivery devices: Preparation methods and in vitro release characterization," Int J Pharmaceutics 87:21-29 (1992).
Illum et al., "Hyaluronic acid ester microspheres as a nasal delivery system for insulin," J Controlled Release 29(1-2):133-141 (1994).
Kubler et al., "Bone Morphogenetic Protein-Mediated Interaction of Periosteum and Diaphysis," Clin Osteoped Rel Res 258:279-94 (1990).

(Continued)

*Primary Examiner*—Cecilia Tsang
*Assistant Examiner*—Christina Bradley
(74) *Attorney, Agent, or Firm*—Finnegan, Henderson, Farabow, Garrett & Dunner, LLP

(57) ABSTRACT

An injectable formulation is disclosed for delivery of osteogenic proteins. The formulation comprises a pharmaceutically acceptable admixture of an osteogenic protein; and formulations comprising osteogenic protein, hyaluronic acid derivatives and tricalcium phosphate are also disclosed. Methods for formulating porous injectable gels and pastes from hyaluronic acid are also disclosed.

15 Claims, 4 Drawing Sheets

OTHER PUBLICATIONS

Solchaga et al., "Hyaluronic Acid-Based Polymers as Cell Carriers for Tissue-Engineered Repair of Bone and Cartilage," J Orthopaedic Res 17:205-213 (1999).

Urist et al., "Bone Regeneration under the Influence of a Bone Morphogenetic Protein (BMP) Beta Tricalcium Phosphate (TCP) Composite in Skull Trephine Defects in Dogs," Clin. Orthoped. Rel. Res., 214:295-304 (1986).

Urist et al., β-tricalcium Phosphate Delivery System for Bone Morphogenetic Protein, Clin. Orthoped. Related Res., 187:227-280 (1984).

Vercruysse et al., "Hyaluronate Derivatives in Drug Delivery," Crit Revs Ther Drug Carriers 15(5):513-15 (1997).

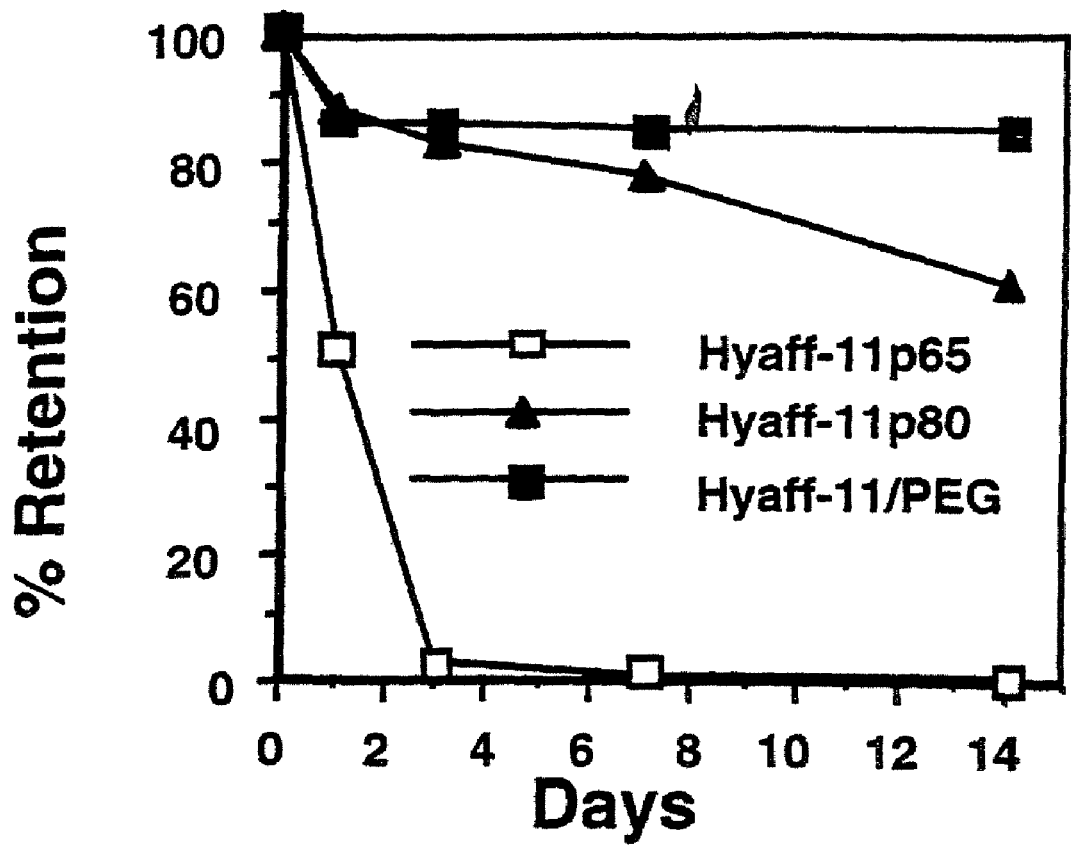
Figure 1: In vitro release kinetics of $^{125}$I-rhBMP-2 in gels of Hyaff-11/PEG, Hyaff-11p80, Hyaff-11p65.

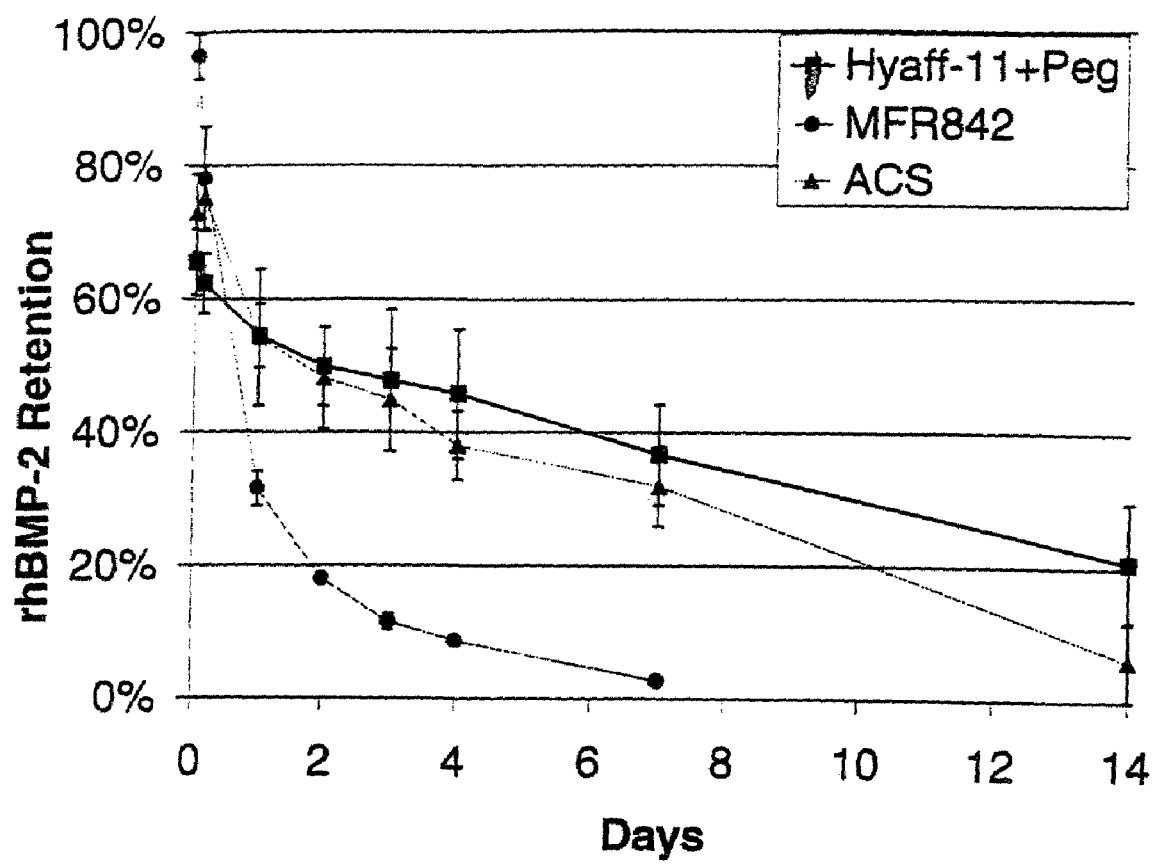
Figure 2: In vivo retention of $^{125}$I-rhBMP-2 in Hyaff-11/PEG, ACS, and buffer.

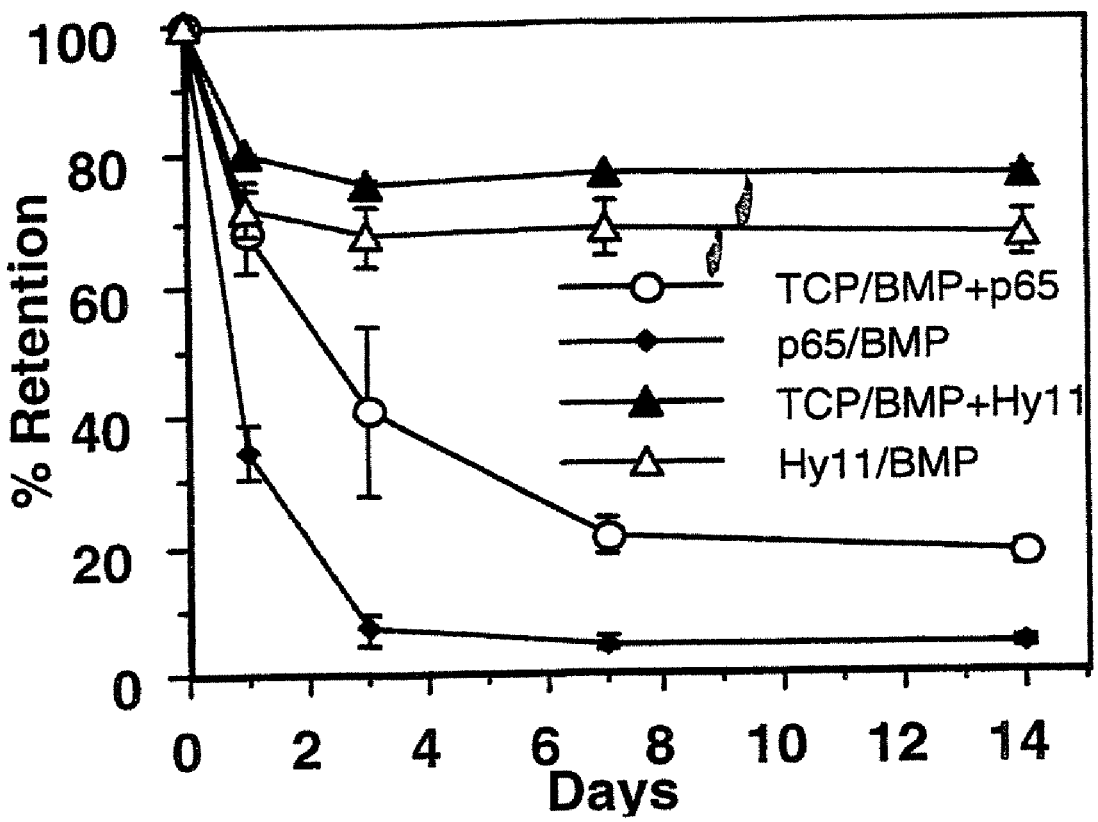
Figure 3. In vitro release kinetics of $^{125}$I-rhBMP-2

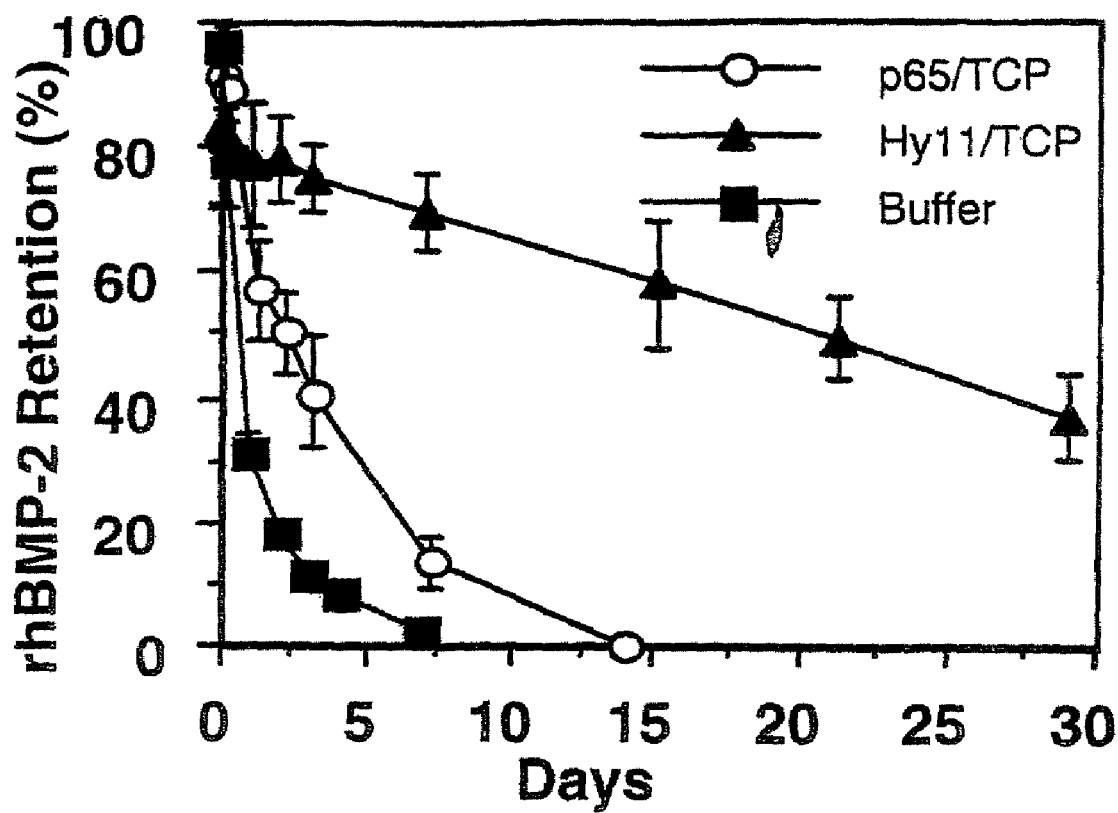
Figure 4. In vivo biodistribution of $^{125}$I-rhBMP-2

INJECTABLE CARRIER FORMULATIONS OF HYALURONIC ACID DERIVATIVES FOR DELIVERY OF OSTEOGENIC PROTEINS

RELATED APPLICATIONS

This application is a continuation of application Ser. No. 09/687,281, filed Oct. 13, 2000, now U.S. Pat. No. 7,189,392, issued on Mar. 13, 2007, which claims the benefit of U.S. Provisional Application No. 60/159,674 filed on Oct. 15, 1999 and U.S. Provisional Application No. 60/185,587 filed on Feb. 28, 2000, all of which are incorporated herein by reference.

BACKGROUND OF THE INVENTION

The subject invention relates to the field of osteogenic proteins and pharmaceutical formulations thereof. More particularly, the subject invention involves injectable pharmaceutical formulations comprising hyaluronic acid derivatives and osteogenic proteins. The invention further provides methods for formulating porous injectable gels and pastes from hyaluronic acid.

Osteogenic proteins are those proteins capable of inducing, or assisting in the induction of, cartilage and/or bone formation. Many such osteogenic proteins have in recent years been isolated and characterized, and some have been produced by recombinant methods. For example, so-called bone morphogenic proteins (BMP) have been isolated from demineralized bone tissue (see e.g. Urist U.S. Pat. No. 4,455,256); a number of such BMP proteins have been produced by recombinant techniques (see e.g. Wang et al. U.S. Pat. No. 4,877,864 and Wang et al. U.S. Pat. No. 5,013,549); a family of transforming growth factors (TGF-α and TGF-β) has been identified as potentially useful in the treatment of bone disease (see e.g. Derynck et al., EP 154,434); a protein designated Vgr-1 has been found to be expressed at high levels in osteogenic cells (see Lyons et al. (1989) Proc. Nat'l. Acad. Sci. USA 86, 4554-4558); and proteins designated OP-1, COP-5 and COP-7 have purportedly shown bone inductive activity (see Oppermann, et al. U.S. Pat. No. 5,001,691).

Various formulations designed to deliver osteogenic proteins to a site where induction of bone formation is desired have been developed. For example, certain polymeric matrices such as acrylic ester polymer (Urist, U.S. Pat. No. 4,526,909) and lactic acid polymer (Urist, U.S. Pat. No. 4,563,489) have been utilized.

A biodegradable matrix of porous particles for delivery of an osteogenic protein designated as OP is disclosed in Kuber A. Sampath, U.S. Pat. No. 5,108,753.

Brekke et al., U.S. Pat. Nos. 4,186,448 and 5,133,755 describe methods of forming highly porous biodegradable materials composed of polymers of lactic acid ("OPLA").

Okada et al., U.S. Pat. No. 4,652,441, U.S. Pat. No. 4,711,782, U.S. Pat. No. 4,917,893 and U.S. Pat. No. 5,061,492 and Yamamoto et al., U.S. Pat. No. 4,954,298 disclose a prolonged-release microcapsule comprising a polypeptide drug and a drug-retaining substance encapsulated in an inner aqueous layer surrounded by a polymer wall substance in an outer oil layer.

Yamazaki et al., *Clin. Orthop. and Related Research*, 234: 240-249 (1988) disclose the use of implants comprising 1 mg of bone morphogenetic protein purified from bone and 5 mg of Plaster of Paris. U.S. Pat. No. 4,645,503 discloses composites of hydroxyapatite and Plaster of Paris as bone implant materials.

Collagen matrices have also been used as delivery vehicles for osteogenic proteins (see e.g. Jeffries, U.S. Pat. No. 4,394,370).

SUMMARY OF THE INVENTION

The present invention provides injectable formulations for delivery of osteogenic proteins. In one embodiment the composition comprises the osteogenic protein and hyaluronic acid esters. In another embodiment, the composition may further include tricalcium phosphate. The injectable formulations of the invention allows for closed fracture repair and other skeletal tissue without an open reduction procedure as is necessary with implantable devices.

The present invention further provides methods for preparing injectable gels or pastes useful as a carrier for osteogenic proteins by transforming various non-woven pads and sponges of hyaluronic acid benzyl ester into injectable gel or paste formulations by hydration or solvent addition. In another embodiment, the invention comprises compositions comprising the transformed injectable gel or paste formulations.

The methods and compositions of the present invention are useful for the preparation of formulations of osteoinductive proteins which can be used, among other uses, to promote the formation of cartilage and/or bone, for repair of tissue damage and fractures. The invention further provides methods for treating patients in need of cartilage and/or bone repair and/or growth.

BRIEF DESCRIPTION OF THE DRAWINGS

FIG. 1 sets forth in vitro release kinetics of $^{125}$I-rhBMP-2 in HYAFF® gels.

FIG. 2 sets forth in vivo retention of $^{125}$I-rhBMP-2 in HYAFF®-11/PEG, ACS, and buffer.

FIG. 3 sets forth in vitro release kinetics of $^{125}$I-rhBMP-2 in HYAFF® gels/TCP.

FIG. 4 sets forth in vivo biodistribution of $^{125}$I-rhBMP-2.

DETAILED DESCRIPTION OF THE INVENTION

The invention provides injectable formulations for delivery of osteogenic proteins. The compositions comprise an injectable formulation of hyaluronic acid esters and osteogenic protein. The present invention further provides processes for preparing injectable gel or paste formulations by transforming various non-woven pads and sponges of hyaluronic acid benzyl ester by hydration or solvent addition yielding gels with in vivo residence times from days to up to several months. Total or partial esters of hyaluronic acid are described in U.S. Pat. No. 5,336,767. Partial esters of HYAFF® solids are transformed into gels using aqueous buffer or organic solvents (such as N-methyl pyrrolidinone, dimethyl sulfoxide, etc), while complete esters of HYAFF® solids are transformed into gels using organic solvents. In other embodiments pore formers may be introduced to the solubilized carriers to increase porosity. The addition of pore formers would allow in situ pore formation after injection in vivo by solubilization of pore former and precipitation/phase inversion of carrier. Suitable liquid pore formers include polyethylene glycol or PEG at 10-90% volume per volume ratios) and solid pore formers (such as sodium bicarbonate, sodium chloride, citric acid, sucrose, etc., at 1:1-21:1 pore former:HYAFF® weight per weight ratios) to increase porosity. The gel/paste can also contain TCP (tri-calcium phosphate) particles as a mineral component for example, at 0.1-100% weight per volume range.

The amount, type and size of the pore forming agent is optimized to leave voids sufficient for cell ingrowth into injectable gel when pore forming agent and solvent are extracted from the carrier in vivo by solubilization of pore forming agent and precipitation/phase inversion of carrier in situ.

The osteogenic proteins useful with the injectable carriers made in accordance with the subject invention are well known to those skilled in the art and include those discussed above. The preferred osteogenic proteins for use herein are those of the BMP class identified as BMP-1 through BMP-12 in U.S. Pat. No. 4,877,864; U.S. Pat. No. 5,013,649; WO 90/11366 published Oct. 4, 1990; WO 91/18098 published Nov. 28, 1991; WO 93/00432, published Jan. 7, 1993; U.S. Ser. Nos. 08/247,908 and 08/247,904, both filed May 20, 1994; and U.S. Ser. No. 08/217,780, filed on Mar. 25, 1994. The disclosure of the above publications are hereby incorporated by reference. The most preferred is BMP-2, the full length cDNA sequence of which is described in detail in the '649 patent. Of course, combinations of two or more of such osteogenic proteins may be used, as may fragments of such proteins that also exhibit osteogenic activity. Such osteogenic proteins are known to be homodimeric species, but also exhibit activity as mixed heterodimers. Heterodimeric forms of osteogenic proteins may also be used in the practice of the subject invention. BMP heterodimers are described in WO93/09229, the disclosure of which is hereby incorporated by reference. Recombinant proteins are preferred over naturally occurring isolated proteins. The amount of osteogenic protein useful herein is that amount effective to stimulate increased osteogenic activity of infiltrating progenitor cells, and will depend upon the size and nature of defect being treated as well as the carrier being employed.

The formulations may be injected for example into tendons, damaged cartilage tissue, ligaments, and/or their attachment sites to bones. Injectable formulations may also find application to other bone sites such as bone cysts, bone defects, intraosseous sites and closed fractures.

The dosage regimen will be determined by the clinical indication being addressed, as well as by various patient variables (e.g. weight, age, sex) and clinical presentation (e.g. extent of injury, site of injury, etc.). In general, the dosage of osteogenic protein will be in the range of from about 0.1 to 4 mg/ml.

The injectable osteogenic protein formulations may be provided to the clinic as a single formulation, or the formulation may be provided as a multicomponent kit wherein, e.g. the osteogenic protein is provided in one vial and the injectable hyaluronic paste is provided separately.

The compositions of the subject invention allow therapeutically effective amounts of osteoinductive protein to be delivered to an injury site where cartilage and/or bone formation is desired. The formulations may be used as a substitute for autologous bone graft in fresh and non-union fractures, spinal fusions, and bone defect repair in the orthopaedic field; in cranio/maxillofacial reconstructions; for prosthesis integration, especially as a surface coating to improve fixation of prosthetic implants such as hydroxyapatite coated prostheses; in osteomyelitis for bone regeneration; and in the dental field for augmentation of the alveolar ridge and periodontal defects and tooth extraction sockets. The methods and formulations of the present invention may be useful in the treatment and/or prevention of osteoporosis, or the treatment of osteoporotic or osteopenic bone. In another embodiment, formulations of the present invention may be used in the process known as distraction osteogenesis. When used to treat osteomyelitis or for bone repair with minimal infection, the osteogenic protein may be used in combination with porous microparticles and antibiotics, with the addition of protein sequestering agents such as alginate, cellulosics, especially carboxymethylcellulose, diluted using aqueous glycerol. The antibiotic is selected for its ability to decrease infection while having minimal adverse effects on bone formation. Preferred antibiotics for use in the devices of the present invention include vancomycin and gentamycin. The antibiotic may be in any pharmaceutically acceptable form, such as vancomycin HCl or gentamycin sulfate. The antibiotic is preferably present in a concentration of from about 0.1 mg/mL to about 10.0 mg/mL. The traditional preparation of formulations in pharmaceutically acceptable form (i.e. pyrogen free, appropriate pH and isotonicity, sterility, etc.) is well within the skill in the art and is applicable to the formulations of the invention.

Hyaluronic derivative compositions of the invention prepared by hydration or solvent addition of insoluble or partially soluble non-woven pads or sponges may also be utilized in combination with other drugs, growth factors, peptides, proteins, cytokines, oligonucleotides antisense oligonucleotides, DNA and polymers. These compounds may be added by mixing them with the carriers. Or by covalent attachment to the polymer carriers. The hyaluronic derivative compositions may also be used with DNA encoding for BMPs and cells transduced or transfected with genes encoding BMP proteins.

The following examples are illustrative of the present invention and are not limiting in any manner. Modifications, variations and minor enhancements are contemplated and are within the present invention.

Example 1

Preparation of Injectable Hyaluronic Acid Esters

The starting HYAFF® hyaluronic acid (Fidia Advanced Biopolymers, Abano Terme, Italy) materials are solids such as non-woven pads, felts, sheets, powders, sponges, and microspheres. The HYAFF® materials are esters of hyaluronic acid exhibiting various ester moities (e.g., benzyl, ethyl, propyl pentyl or larger molecules such as hydrocortisone or methyl prednisone, etc.) as well as various degrees of esterification (i.e., partial esters or complete esters). Partial esters of HYAFF® are designated by percent esterification ranging from 50-99% (e.g., HYAFF®-11p65, HYAFF®-11p80, etc.), while complete esters are 100% esters of hyaluronic acid (e.g., HYAFF®-11). HYAFF® gel classification used in supporting data is as follows and is followed by examples of select formulations:

HYAFF®-11 gel: HYAFF®-11 non-woven pad transformed into gel with organic solvent to yield 10% solids HYAFF®-11/bicarbonate gel: HYAFF®-11 gel mixed with sodium bicarbonate as pore former at 15:1 (w/w) bicarbonate to HYAFF®-11

HYAFF®-11/PEG gel: HYAFF®-11 gel mixed with polyethylene glycol (200 mw) as pore former at 33-50% (v/v) range HYAFF®-11/TCP gel: HYAFF®-11 gel mixed with 30% w/v TCP HYAFF®-11/bicarbonate/TCP gel: HYAFF®-11/bicarbonate gel mixed with 30% w/v TCP HYAFF®-11/PEG/TCP gel: HYAFF®-11/PEG gel mixed with 30% w/v TCP HYAFF®-11p80 gel: HYAFF®-11p80 non-woven pad transformed into gel with organic solvent to yield 5% solids HYAFF®-11p65 gel: HYAFF®-11p65 non-woven pad hydrated with aqueous buffer to yield 6-15% solids HYAFF®-11p65/TCP gel: HYAFF®-11p65 gel mixed with 30% w/v TCP HYAFF®-11p65 non-woven pads were hydrated with glutamic acid buffer (pH 4.5) containing rhBMP-2 (0.1 mg/mL final conc.) to yield either 6%-15% solids (w/v) and mixed thoroughly to form a paste. HYAFF®-11p80 and HYAFF®-11 non-woven pads were solubilized in N-methylpyrrolidinone (NMP) or dimethyl sulfoxide (DMSO) to yield a 1-30% w/v solution. These solutions were then mixed with either rhBMP-2-containing buffer (10% v/v, 0.1 mg/mL rhBMP-2), or lyophilized rhBMP-2 (0.1 mg/mL) followed by the addition of various pore formers (polyethylene glycol, sodium bicarbonate, sucrose, NaCl, citric acid) and tricalcium phosphate (TCP). Particle size of solid pore formers and TCP used was <600 um, preferably <200 um. Liquid pore formers such as PEG (200 mw) were mixed at 10-90% v/v ratios, and solid pore formers were mixed at 9:1-21:1 (w/w) pore former to carrier ratios. TCP was mixed at 0.1-30% (w/v). TCP (45-125 micron particle size) was mixed thoroughly into rhBMP-2/HYAFF®-11 or rhBMP-2/HYAFF®-11p65 gel at 30% (w/v). Separately, rhBMP-2 was adsorbed onto TCP first, followed by mixing with HYAFF®-11 or HYAFF®-11p65 gel. Formulations were chosen based on injectability through an 18 g needle. Microstructure was characterized by scanning electron microscopy (SEM).

SEMS revealed varying degrees of pore structure and porosity. HYAFF®-11p65 6% gel exhibited longer fibers than the 15% formulation; with both displaying a high level of porosity. Both HYAFF®-11 and HYAFF®-11p80 gels showed minimal pore structure and porosity, whereas those carriers with pore formers displayed a high level of porosity. Pore formers and/or additives that yielded injectable mixtures were PEG, sodium bicarbonate and TCP.

Example 2

In Vitro Release Kinetics rhBMP-2 was radiolabeled with $^{125}$I using the Iodogen method (Pierce) and used as a tracer for 0.1 mg/ml rhBMP-2 delivered in 100 ul HYAFF®-11p65 gel, HYAFF®-11p80 gel, HYAFF®-11 gel and HYAFF®-11/PEG (n=4). $^{125}$I-rhBMP-2 loaded samples (50,000 cpm/sample) were incubated in 1 ml fetal calf serum (Hyclone) at 37° C. on a shaker, and radioactivity of the carrier measured up to 14 days using a gamma counter. Fresh serum was replaced after each time point. $^{125}$I-rhBMP-2 release from injectable formulations were compared to those of implantable sponges and pads of HYAFF®-11 and HYAFF®-11p80.

Auto cross-linked polysaccharide form of derivitized hyaluronic acid, ACP gel, is used for the in vitro release study and the rat ectopic assay. For the in vitro release study, 2 ml ACP gel is mixed with 1.53 mg rhBMP-2 cake (which corresponds to 0.2 mg actual rhBMP-2 at 8 mg rhBMP-2 per 61 mg cake weight) and $^{125}$I-rhBMP-2 (100 μl total, 20 μCi/200 W gel) and drawn up into 1 ml syringes resulting in approximately 10% gel dilution. ACP gel for the rat ectopic study does not contain the tracer but is diluted with MRF-00906 buffer. 200 μl injections are performed using a 22 gauge needle. The final concentration of rhBMP-2 will be 0.1 mg/ml, or 20 μg per 200 μL injection. The final concentration of $^{125}$I-rhBMP-2 will be approximately 20 μCi per 200 μl injection. The ACP gel will be injected at room temperature.

In vitro release kinetics showed greatest retention of rhBMP-2 over the 2 weeks in the HYAFF®-11/PEG gel followed by HYAFF®-11p80 gel and HYAFF®-11 gel (FIG. 1). HYAFF®-11p65 gel released rhBMP-2 the fastest. Sponges and pads of HYAFF®-11 and HYAFF®-11p80 retained less rhBMP-2 than HYAFF®-11/PEG or HYAFF®-11p80 gel, but more than HYAFF®-11p65. Addition of TCP to HYAFF®-11 gel increased rhBMP-2 retention. The release profile in all carriers exhibited moderate to rapid burst release followed by a slow, sustained release of rhBMP-2. All HYAFF®-11 and HYAFF®-11p80 gel formulations retained rhBMP-2 well (>50% remaining after 14 days) except HYAFF®-11p65.

Example 3

Rat Ectopic Assay

HYAFF®-11 based gels (200 ul/site, n=6) with 0.1 mg/ml rhBMP-2 were injected subcutaneously (ventral thorax) or injected intramuscularly (quadriceps) in 3-4 week old male Long Evans rats. Rats were sacrificed after 2 weeks and bone formation in the explants analyzed histologically using Goldner's trichrome stain. Bone scores (0=no bone, 5=100% bone) were assigned based on histomorphometry. Total bone (mm$^3$) was calculated using explant size and bone score. Radiographs of explants were also taken.

All HYAFF®-11 based gels formed significant ectopic bone in the rat model (Table 1) in the presence of rhBMP-2, although differences in bone formation existed between carrier types as confirmed by radiographs and histology. HYAFF®-11p65 at varying doses (0.1-1.5 mg/mL) of rhBMP-2 exhibited a dose dependent increase in bone formation (and bone score) but was inconsistent in explant size which yielded less total bone (0.1 mg/mL rhBMP-2 data shown). HYAFF®-11p80 explants were large but had a lower bone score, while HYAFF®-11 showed good bone score and total bone. HYAFF®-11/PEG and HYAFF®-11/sodium bicarbonate radiographically showed equivalent radioopacity as those of HYAFF®-11 and HYAFF®-11p80. Histologically, both HYAFF®-11 and HYAFF®-11p80 carriers showed residual remaining matrix due to their slow degradation rates, although HYAFF®-11p65 completely degraded by 2 weeks. Bone formed within pores, shown by mineralizing osteoblasts as well as through a cartilage intermediate. Addition of TCP to HYAFF®-11 gel with or without pore formers also showed comparable radiographic evidence of bone formation as those of other HYAFF® based gels.

TABLE 1

Histomorphometry results of rat ectopic bone formation assay.

| Group | Bone score SQ | IM | Total bone SQ | (mm$^3$) IM |
|---|---|---|---|---|
| HYAFF ®-11p65 | 2.70 | 3.88 | 79 | 172 |
|  | (1.40) | (1.65) | (20) | (33) |
| HYAFF ®-11p80 | 1.83 | 1.83 | 140 | 314 |
|  | (0.68) | (0.68) | (76) | (179) |
| HYAFF ®-11 | 2.50 | 3.25 | 228 | 219 |
|  | (1.00) | (0.96) | (132) | (223) |

Example 4

In Vivo Biodistribution

Retention of rhBMP-2 within each carrier was analyzed in vivo using a rabbit ulna fracture model. Bilateral 0.5 mm osteotomy defects were created in the ulna of New Zealand White rabbits and 150 uL rhBMP-2/carrier injected into the defect (n=8/group). Gels were loaded with 40 uCi $^{125}$I labeled rhBMP-2 and 0.67 mg/ml unlabeled rhBMP-2. Amount of radioactivity retained at the fracture site was measured by gamma scintigraphy as a function of time.

In vivo biodistribution of rhBMP-2 from HYAFF®-11/PEG gel in the rabbit ulna fracture model showed better retention of rhBMP-2 than absorbable collagen sponge (ACS) and buffer carrier (MFR-842) (FIG. 2). HYAFF®-11/PEG retained approximately 40% rhBMP-2 after 7 days. HYAFF®-11p65 gel showed poorer retention of rhBMP-2 than HYAFF®-11/PEG gel, but displayed comparable fracture callus radiographically.

Example 5

In Vitro Release Kinetics rhBMP-2 was radiolabeled with $^{125}$I using the Iodogen method (Pierce) and used as a tracer for 0.1 mg/ml rhBMP-2 delivered in 100 uL HYAFF®-11 gel±TCP and HYAFF®-11p65 gel TCP (n=4). $^{125}$I-rhBMP-2 loaded samples (50,000 cpm/sample) were incubated in 1 mL fetal calf serum (Hyclone) at 37° C. on a shaker, and radioactivity of the carrier measured up to 14 days using a gamma counter. Fresh serum was replaced after 1, 3, 7, and 14 days.

Addition of TCP enhanced retention of rhBMP-2 over the course of 2 weeks in both HYAFF®-11 and HYAFF®-11p65 gels (FIG. 3). HYAFF®-11/TCP retained the most rhBMP-2, followed by HYAFF®-11, HYAFF®-11p65/TCP, and HYAFF®-11p65. HYAFF®-11 retained more rhBMP-2 than HYAFF®-11p65 due to its hydrophobicity and insolubility. Preadsorbing rhBMP-2 on TCP increased rhBMP-2 retention in HYAFF®-11 gel, as opposed to mixing rhBMP-2 into the HYAFF®-11 phase. Preadsorbing or mixing rhBMP-2 into either TCP or HYAFF®-11p65 phase resulted in similar rhBMP-2 retention, both of which were greater than HYAFF®-11p65 without TCP.

Example 6

In Vivo Biodistribution and Efficacy

Retention of rhBMP-2 within HYAFF®-11/TCP and HYAFF®-11p65/TCP was analyzed in vivo using a rabbit ulna fracture model. Bilateral 0.5 mm osteotomy defects were created in the ulna of New Zealand White rabbits (n=3/carrier) and 150 uL carrier or buffer (0.67 mg/mL rhBMP-2) injected around the defect. 20 uCi $^{125}$I-rhBMP-2 was used as a tracer. Amount of radioactivity left within each carrier at the fracture site was measured by gamma scintigraphy over the course of several weeks and in vivo rhBMP-2 retention calculated over time. Fracture repair efficacy was analyzed in these rabbits (n=8) by torsional biomechanical testing after a 4 week sacrifice to obtain maximum torque. Contralateral limbs served as surgical controls.

In vivo retention of rhBMP-2 at the rabbit ulna fracture site showed a similar pattern as that of the in vitro study (FIG. 4). HYAFF®-11/TCP gel (rhBMP-2 adsorbed to TCP phase first) exhibited the greatest retention (40% remaining after 4 weeks) followed by HYAFF®-11p65/TCP gel (rhBMP-2 undetectable at 14 days) and buffer (undetectable at 7 days). rhBMP-2 accelerated fracture healing when delivered in HYAFF®-11p65/TCP or HYAFF®-11p65 gel. Maximum torque (N-m) for HYAFF®-11p65/TCP and HYAFF®-11p65 were significantly greater than their contralateral surgical controls (85.6% and 96.9%, respectively) but not statistically different from each other (Table 2).

TABLE 2

Maximum torque (N-m) of rabbit ulna defects

| Carrier | rhBMP-2 | Control | P value |
|---|---|---|---|
| P65 | 0.571 ± 0.225 | 0.290 ± 0.158 | 0.0001 |
| P65/TCP | 0.475 ± 0.197 | 0.256 ± 0.087 | 0.0091 |

The foregoing descriptions detail presently preferred embodiments of the present invention. Numerous modifications and variations in practice thereof are expected to occur to those skilled in the art upon consideration of these descriptions. Those modifications are believed to be encompassed within the claims appended hereto.

What is claimed is:

1. A method for promoting bone, cartilage, or tendon formation in a patient comprising injecting an osteogenic composition through the skin of the patient to a site in need of bone formation, wherein the composition comprises
    (a) an osteogenic protein,
    (b) an injectable hyaluronic acid ester, and
    (c) a pore former selected from a liquid pore former or sodium bicarbonate.

2. The method of claim 1, wherein the composition is administered by intraosseous injection.

3. The method of claim 1, wherein the method of promoting bone formation comprises distraction osteogenesis.

4. The method of claim 1, wherein the method of promoting bone formation comprises repair of a bone defect.

5. The method of claim 4, wherein the repair of a bone defect comprises closed fracture repair.

6. The method of claim 4, wherein the bone defect is a bone fracture.

7. The method of claim 4, wherein the bone defect is osteoporosis.

8. The method of claim 4, wherein the bone defect is a non-union bone fracture.

9. The method of claim 1, wherein the osteogenic protein is selected from the group consisting of Bone Morphogenic Protein (BMP)-2, BMP-4, BMP-5, BMP-6, BMP-7, BMP-8, BMP-9, BMP-10, BMP-11, and BMP-12.

10. The method of claim 1, wherein the hyaluronic acid ester is selected from the group consisting of 100% esterified benzyl ester hyaluronic acid ester, 80% esterified benzyl ester hyaluronic acid ester, and 65% esterified benzyl ester hyaluronic acid ester.

11. The method of claim 1, wherein the composition further comprises tricalcium phosphate (TCP).

12. A method for promoting the attachment of ligament to bone in a patient comprising injecting an osteogenic composition through the skin of the patient to a site in need of attachment, wherein the composition comprises
    (a) an osteogenic protein,
    (b) an injectable hyaluronic acid ester, and
    (c) a pore former selected from a liquid pore former or sodium bicarbonate.

13. The method of claim 12, wherein the osteogenic protein is selected from the group consisting of Bone Morphogenic Protein (BMP)-2, BMP-4, BMP-5, BMP-6, BMP-7, BMP-8, BMP-9, BMP-10, BMP-11, and BMP-12.

14. The method of claim 12, wherein the hyaluronic acid ester is selected from the group consisting of 100% esterified benzyl ester hyaluronic acid ester, 80% esterified benzyl ester hyaluronic acid ester, and 65% esterified benzyl ester hyaluronic acid ester.

15. The method of claim 12, wherein the composition further comprises tricalcium phosphate (TCP).

* * * * *